United States Patent [19]
Davis et al.

[11] Patent Number: 5,643,755
[45] Date of Patent: Jul. 1, 1997

[54] NUCLEIC ACID ENCODING TIE-2 LIGAND

[75] Inventors: Samuel Davis, New York; Thomas Aldrich, Ossining; George D. Yancopoulos, Yorktown Heights, all of N.Y.

[73] Assignee: Regeneron Pharmaceuticals Inc., Tarrytown, N.Y.

[21] Appl. No.: 319,932

[22] Filed: Oct. 7, 1994

[51] Int. Cl.$^6$ .................... C12N 15/12; C07K 14/705
[52] U.S. Cl. .................. 435/69.5; 435/70.1; 435/348; 435/252.3; 435/320.1; 435/325; 435/365; 435/365.1; 935/22; 935/69; 935/70; 935/72; 536/23.1; 536/23.5; 536/24.3; 536/24.31
[58] Field of Search ................ 536/23.1, 23.5; 435/69.5, 70.1, 172.3, 240.3, 240.2, 252.3, 320.1; 530/350; 935/22, 52, 72, 69, 70

[56] References Cited

PUBLICATIONS

Derynck et al. 1990, Biochemistry, vol. 29, pp. 10225–10233.

Weissenbach et al. 1980, Proc. Natl. Acad, Sci, vol. 77, No. 12, pp. 7152–7156.

*Primary Examiner*—John Ulm
*Assistant Examiner*—Prema Mertz
*Attorney, Agent, or Firm*—Gail M. Kempler; Robert J. Cobert

[57] ABSTRACT

The present invention provides for TIE-2 ligand substantially free of other proteins. The invention also provides for an isolated nucleic acid molecule encoding TIE-2 ligand. In addition, the invention provides for a receptor body which specifically binds TIE-2 ligand. The invention also provides an antibody which specifically binds TIE-2 ligand. The invention further provides for therapeutic compositions as well as a method of blocking blood vessel growth, a method of promoting neovascularization and a method of promoting the growth or differentiation of a cell expressing the TIE-2 receptor.

11 Claims, 2 Drawing Sheets r EHK-1 ecto / h IgG1 Fc
Gelfoam ( 6 ug)

r TIE-2 ecto / h IgG1 Fc
Gelfoam ( 6 ug)

NUCLEIC ACID ENCODING TIE-2 LIGAND

Throughout this application various publications are referenced. The disclosures of these publications in their entireties are hereby incorporated by reference into this application.

INTRODUCTION

The present invention relates generally to the field of genetic engineering and more particularly to genes for receptor tyrosine kinases and their cognate ligands, their insertion into recombinant DNA vectors, and the production of the encoded proteins in recipient strains of microorganisms and recipient eukaryotic cells. More specifically, the present invention is directed to a novel ligand, known as the TIE-2 ligand, that binds and activates the TIE-2 receptor, as well as methods of making and using the TIE-2 ligand. The invention further provides nucleic acid sequences encoding TIE-2 ligand, and methods for the generation of nucleic acids encoding TIE-2 ligand and their gene products. The TIE-2 ligand, as well as nucleic acids encoding it, may be useful in the diagnosis and treatment of certain diseases involving endothelial cells and associated TIE receptors, such as neoplastic diseases involving tumor angiogenesis, wound healing, thromboembolic diseases, atherosclerosis and inflammatory diseases. More generally, the TIE-2 ligand may be used to promote the growth, survival and/or differentiation of cells expressing the TIE-2 receptor. The TIE-2 ligand may be used for the in vitro maintenance of TIE-2 receptor expressing cells in culture. Cells and tissues expressing TIE-2 receptor include, for example, cardiac and vascular endothelial cells, lens epithelium and heart epicardium. Alternatively, the ligand may be used to support cells which are engineered to express TIE-2 receptor. Further, the TIE-2 ligand and its cognate receptor may be used in assay systems to identify agonists or antagonists of the TIE-2 receptor.

BACKGROUND OF THE INVENTION

The cellular behavior responsible for the development, maintenance, and repair of differentiated cells and tissues is regulated, in large part, by intercellular signals conveyed via growth factors and similar ligands and their receptors. The receptors are located on the cell surface of responding cells and they bind peptides or polypeptides known as growth factors as well as other hormone-like ligands. The results of this interaction are rapid biochemical changes in the responding cells, as well as a rapid and a long-term readjustment of cellular gene expression. Several receptors associated with various cell surfaces may bind specific growth factors.

The phosphorylation of tyrosines on proteins by tyrosine kinases is one of the key modes by which signals are transduced across the plasma membrane. Several currently known protein tyrosine kinase genes encode transmembrane receptors for polypeptide growth factors and hormones such as epidermal growth factor (EGF), insulin, insulin-like growth factor-I (IGF-I), platelet derived growth factors (PDGF-A and -B), and fibroblast growth factors (FGFs). (Heldin et al., Cell Regulation, 1: 555–566 (1990); Ullrich, et al., Cell, 61: 243–54 (1990)). In each instance, these growth factors exert their action by binding to the extracellular portion of their cognate receptors, which leads to activation of the intrinsic tyrosine kinase present on the cytoplasmic portion of the receptor. Growth factor receptors of endothelial cells are of particular interest due to the possible involvement of growth factors in several important physiological and pathological processes, such as vasculogenesis, angiogenesis, atherosclerosis, and inflammatory diseases. (Folkman, et al. Science, 235: 442–447 (1987)). Also, the receptors of several hematopoietic growth factors are tyrosine kinases; these include c-fms, which is the colony stimulating factor 1 receptor, Sherr, et al., Cell, 41: 665–676 (1985), and c-kit, a primitive hematopoietic growth factor receptor reported in Huang, et al., Cell, 63: 225–33 (1990).

The receptor tyrosine kinases have been divided into evolutionary subfamilies based on the characteristic structure of their ectodomains. (Ullrich, et al. Cell, 61: 243–54 (1990)). Such subfamilies include, EGF receptor-like kinase (subclass I) and insulin receptor-like kinase (subclass II), each of which contains repeated homologous cysteine-rich sequences in their extracellular domains. A single cysteine-rich region is also found in the extracellular domains of the eph-like kinases. Hirai, et al., Science, 238: 1717–1720 (1987); Lindberg, et al. Mol. Cell. Biol., 10: 6316–24 (1990); Lhotak, et al., Mol. Cell. Biol. 11: 2496–2502 (1991). PDGF receptors as well as c-fms and c-kit receptor tyrosine kinases may be grouped into subclass III; while the FGF receptors form subclass IV. Typical for the members of both of these subclasses are extracellular folding units stabilized by intrachain disulfide bonds. These so-called immunoglobulin (Ig)-like folds are found in the proteins of the immunoglobulin superfamily which contains a wide variety of other cell surface receptors having either cell-bound or soluble ligands. Williams, et al., Ann. Rev. Immunol., 6: 381–405 (1988).

Receptor tyrosine kinases differ in their specificity and affinity. In general, receptor tyrosine kinases are glycoproteins, which consist of (1) an extracellular domain capable of binding the specific growth factor(s); (2) a transmembrane domain which usually is an alpha-helical portion of the protein; (3) a juxtamembrane domain where the receptor may be regulated by, e.g., protein phosphorylation; (4) a tyrosine kinase domain which is the enzymatic component of the receptor; and (5) a carboxyterminal tail which in many receptors is involved in recognition and binding of the substrates for the tyrosine kinase.

Processes such as alternative exon splicing and alternative choice of gene promoter or polyadenylation sites have been reported to be capable of producing several distinct polypeptides from the same gene. These polypeptides may or may not contain the various domains listed above. As a consequence, some extracellular domains may be expressed as separate, secreted proteins and some forms of the receptors may lack the tyrosine kinase domain and contain only the extracellular domain inserted in the plasma membrane via the transmembrane domain plus a short carboxyl terminal tail.

A gene encoding an endothelial cell transmembrane tyrosine kinase, originally identified by RT-PCR as an unknown tyrosine kinase-homologous cDNA fragment from human leukemia cells, was described by Partanen, et al., Proc. Natl. Acad. Sci. USA, 87: 8913–8917 (1990). This gene and its encoded protein are called "tie" which is an abbreviation for "tyrosine kinase with Ig and EGF homology domains." Partanen, et al. Mol. Cell. Biol. 12: 1698–1707 (1992).

It has been reported that tie mRNA is present in all human fetal and mouse embryonic tissues. Upon inspection, tie message has been localized to the cardiac and vascular endothelial cells. tie mRNA has been localized to the endothelia of blood vessels and endocardium of 9.5 to 18.5 day old mouse embryos. Enhanced tie expression was shown during neovascularization associated with developing ovarian follicles and granulation tissue in skin wounds. Korhonen, et al. Blood 80: 2548–2555 (1992). Thus tie has been suggested to play a role in angiogenesis, which is important for developing treatments for solid tumors and several other angiogenesis-dependent diseases such as diabetic retinopathy, psoriasis, atherosclerosis and arthritis.

Two structurally related rat TIE receptor proteins have been reported to be encoded by distinct genes, termed tie-1 and tie-2, with related profiles of expression. Both genes were found to be widely expressed in endothelial cells of embryonic and postnatal tissues. Significant levels of tie-2 transcripts were also present in other embryonic cell populations, including lens epithelium, heart epicardium and regions of mesenchyme. Maisonpierre, et al., Oncogene 8: 1631–1637 (1993).

The predominant expression of the TIE receptor in vascular endothelia suggests that TIE plays a role in the development and maintenance of the vascular system. This could include roles in endothelial cell determination, proliferation, differentiation and cell migration and patterning into vascular elements. In the mature vascular system, TIE could function in endothelial cell survival, maintenance and response to pathogenic influences.

SUMMARY OF THE INVENTION

The present invention provides for a composition comprising TIE-2 ligand substantially free of other proteins. The invention also provides for an isolated nucleic acid molecule encoding TIE-2 ligand. The isolated nucleic acid may be DNA, cDNA or RNA. The invention also provides for a vector comprising the isolated nucleic acid molecule encoding TIE-2 ligand. The invention further provides for a host-vector system for the production in a suitable host cell of a polypeptide having the biological activity of TIE-2 ligand. The suitable host cell may be bacterial, yeast, insect or mammalian. The invention also provides for a method of producing a polypeptide having the biological activity of TIE-2 ligand which comprises growing cells of the host-vector system under conditions permitting production of the polypeptide and recovering the polypeptide so produced.

In addition, the present invention provides for an antibody which specifically binds TIE-2 ligand. The antibody may be monoclonal or polyclonal. The invention further provides for therapeutic compositions comprising an antibody which specifically binds TIE-2 ligand in a pharmaceutically acceptable vehicle. The invention also provides for a method of blocking blood vessel growth in a mammal by administering an effective amount of a therapeutic composition comprising an antibody which specifically binds TIE-2 ligand in a pharmaceutically acceptable vehicle.

The invention further provides for therapeutic compositions comprising TIE-2 ligand in a pharmaceutically acceptable vehicle. The invention also provides for a method of promoting neovascularization in a patient by administering an effective amount of a therapeutic composition comprising TIE-2 ligand in a pharmaceutically acceptable vehicle. In one embodiment, the method may be used to promote wound healing. In another embodiment, the method may be used to treat ischemia.

Alternatively, the invention provides that the TIE-2 ligand may be conjugated to a cytotoxic agent and a therapeutic composition prepared therefrom. The invention further provides for a receptor body which specifically binds TIE-2 ligand. The invention further provides for therapeutic compositions comprising a receptor body which specifically binds TIE-2 ligand in a pharmaceutically acceptable vehicle. The invention also provides for a method of blocking blood vessel growth in a mammal by administering an effective amount of a therapeutic composition comprising a receptor body which specifically binds TIE-2 ligand in a pharmaceutically acceptable vehicle.

BRIEF DESCRIPTION OF THE FIGURES

FIG. 1A: embryos treated with EHK-1 RB (rEHK-1 ecto/h IgG1 Fc) were viable and possessed normally developed blood vessels in their surrounding CAM. FIG. 1B: all embryos treated with TIE-2 RB (r TIE-2 ecto/h IgG1 Fc) were dead, diminished in size and were almost completely devoid of surrounding blood vessels.

DETAILED DESCRIPTION OF THE INVENTION

Figure 1A:
FIGS. 1A and 1B—TIE-2 receptorbody (TIE-2 RB) inhibits the development of blood vessels in the embryonic chicken chorioallantoic membrane (CAM). A single piece of resorbable gelatin foam (Gelfoam) soaked with 6 µg of RB was inserted immediately under the CAM of 1-day chick embryos. After 3 further days of incubation, 4 day old embryos and surrounding CAM were removed and examined.

As described in greater detail below, applicants have isolated, by expression cloning, a novel ligand that binds the TIE-2 receptor. The present invention comprises the TIE-2 ligand as well as its amino acid sequence, which can be obtained using methodology known and available in the art, and also functionally equivalent molecules in which amino acid residues are substituted for residues within the sequence resulting in a silent change. For example, one or more amino acid residues within the sequence can be substituted by another amino acid(s) of a similar polarity which acts as a functional equivalent, resulting in a silent alteration. Substitutes for an amino acid within the sequence may be selected from other members of the class to which the amino acid belongs. For example, the class of nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, etc.

The present invention also encompasses the nucleotide sequence that encodes the protein described herein as TIE-2 ligand, as well as cells which are genetically engineered to produce the protein, by e.g. transfection, transduction, infection, electroporation, or microinjection of nucleic acid encoding the TIE-2 ligand described herein in a suitable expression vector.

One skilled in the art will also recognize that the present invention encompasses DNA and RNA sequences that hybridize to the deduced TIE-2 ligand encoding sequence, under conditions of moderate stringency, as defined in, for example, Sambrook, et al. Molecular Cloning: A Laboratory Manual, 2 ed. Vol. 1, ppp. 101–104, Cold Spring Harbor Laboratory Press (1989). Thus, a nucleic acid molecule contemplated by the invention includes one having a sequence deduced from the amino acid sequence of TIE-2 ligand prepared as described herein, as well as a molecule having a sequence of nucleic acids that hybridizes to such a nucleic acid sequence, and also a nucleic acid sequence which is degenerate of the above sequences as a result of the genetic code, but which encodes a ligand that binds the TIE-2 receptor.

Any of the methods known to one skilled in the art for the insertion of DNA fragments into a vector may be used to construct expression vectors encoding TIE-2 ligand using appropriate transcriptional/translational control signals and the protein coding sequences. These methods may include in vitro recombinant DNA and synthetic techniques and in vivo recombinations (genetic recombination). Expression of a nucleic acid sequence encoding the TIE-2 ligand or peptide fragments thereof may be regulated by a second nucleic acid sequence so that the protein or peptide is expressed in a host transformed with the recombinant DNA molecule. For example, expression of the TIE-2 ligand described herein may be controlled by any promoter/enhancer element known in the art. Promoters which may be used to control expression of the ligand include, but are not limited to the long terminal repeat as described in Squinto et al., (Cell 65: 1–20 (1991)); the SV40 early promoter region (Bernoist and Chambon, Nature 290: 304–310), the CMV promoter, the M-MuLV 5' terminal repeat, the promoter contained in the 3' long terminal repeat of Rous sarcoma virus (Yamamoto, et al., Cell 22: 787–797 (1980)), the herpes thymidine kinase promoter (Wagner et al., Proc. Natl. Acad. Sci. U.S.A. 78: 144–1445 (1981)), the adenovirus promoter, the regulatory sequences of the metallothioein gene (Brinster et al., Nature 296: 39–42 (1982)); prokaryotic expression vectors such as the β-lactamase promoter (Villa-Kamaroff, et al., Proc. Natl. Acad. Sci. U.S.A. 75: 3727–3731 (1978)), or the tac promoter (DeBoer, et al., Proc. Natl. Acad. Sci. U.S.A. 80: 21–25 (1983)), see also "Useful proteins from recombinant bacteria" in Scientific American, 242: 74–94 (1980); promoter elements from yeast or other fungi such as the Gal 4 promoter, the ADH (alcohol dehydrogenase) promoter, PGK (phosphoglycerol kinase) promoter, alkaline phophatase promoter, and the following animal transcriptional control regions, which exhibit tissue specificity and have been utilized in transgenic animals: elastase I gene control region which is active in pancreatic acinar cells (Swift et al., Cell 38: 639–646 (1984); Ornitz et al., Cold Spring Harbor Symp. Quant. Biol. 50: 399–409 (1986); MacDonald, Hepatology 7: 425–515 (1987); insulin gene control region which is active in pancreatic beta cells (Hanahan, Nature 315: 115–122 (1985)), immunoglobulin gene control region which is active in lymphoid cells (Grosschedl et al., 1984, Cell 38: 647–658; Adames et al., 1985, Nature 318: 533–538; Alexander et al., 1987, Mol. Cell. Biol. 7: 1436–1444), mouse mammary tumor virus control region which is active in testicular, breast, lymphoid and mast cells (Leder et al., 1986, Cell 45: 485–495), albumin gene control region which is active in liver (Pinkert et al., 1987, Genes and Devel. 1: 268–276), alpha-fetoprotein gene control region which is active in liver (Krumlauf et al., 1985, Mol. Cell. Biol. 5: 1639–1648; Hammer et al., 1987, Science 235: 53–58); alpha 1-antitrypsin gene control region which is active in the liver (Kelsey et al, 1987, Genes and Devel. 1: 161–171), beta-globin gene control region which is active in myeloid cells (Mogram et al., 1985, Nature 315: 338–340; Kollias et al., 1986, Cell 46: 89–94); myelin basic protein gene control region which is active in oligodendrocyte cells in the brain (Readhead et al., 1987, Cell 45: 703–712); myosin light chain-2 gene control region which is active in skeletal muscle (Shani, 1985, Nature 314: 283–286), and gonadotropic releasing hormone gene control region which is active in the hypothalamus (Mason et al., 1986, Science 234: 1372–1378). The invention further encompasses the production of antisense compounds which are capable of specifically hybridizing with a sequence of RNA encoding the TIE-2 ligand to modulate its expression. (Ecker, U.S. Pat. No. 5,166,195, issued Nov. 24, 1992).

Thus, according to the invention, expression vectors capable of being replicated in a bacterial or eukaryotic host comprising a nucleic acid encoding TIE-2 ligand as described herein, are used to transfect a host and thereby direct expression of such nucleic acid to produce the TIE-2 ligand, which may then be recovered in biologically active form. As used herein, a biologically active form includes a form capable of binding to the TIE-2 receptor, causing a differentiated function and/or influencing the phenotype of the cell expressing the receptor. Such biologically active forms would, for example, induce phosphorylation of the tyrosine kinase domain of the TIE-2 receptor.

Expression vectors containing the gene inserts can be identified by four general approaches: (a) DNA-DNA hybridization, (b) presence or absence of "marker" gene functions, (c) expression of inserted sequences and (d) PCR detection. In the first approach, the presence of a foreign gene inserted in an expression vector can be detected by DNA-DNA hybridization using probes comprising sequences that are homologous to an inserted TIE-2 ligand encoding gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the nucleic acid encoding the TIE-2 ligand is inserted within the marker gene sequence of the vector, recombinants containing the insert can be identified by the absence of the marker gene function. In the third approach, recombinant expression vectors can be identified by assaying the foreign gene product expressed by the recombinant. Such assays can be based, for example, on the physical or functional properties of the TIE-2 ligand gene product, for example, by binding of the ligand to the TIE-2 receptor or portion thereof which may be tagged with, for example, a detectable antibody or portion thereof or by binding to antibodies produced against the TIE-2 ligand protein or a portion thereof. Cells of the present invention may transiently or, preferably, constitutively and permanently express the TIE-2 ligands as described herein. In the fourth approach, DNA nucleotide primers can be prepared corresponding to tie-2 specific DNA sequence. These primers could then be used to PCR a tie-2 gene fragment. (PCR Protocols: A Guide To Methods and Applications, Edited by Michael A. Innis et al., Academic Press (1990)).

The recombinant ligand may be purified by any technique which allows for the subsequent formation of a stable, biologically active protein. For example, and not by way of limitation, the ligand may be recovered from cells either as soluble proteins or as inclusion bodies, from which they may be extracted quantitatively by 8M guanidinium hydrochloride and dialysis. In order to further purify the ligand, conventional ion exchange chromatography, hydrophobic interaction chromatography, reverse phase chromatography or gel filtration may be used.

In additional embodiments of the invention, the recombinant TIE-2 ligand encoding gene may be used to inactivate or "knock out" the endogenous gene by homologous recombination, and thereby create a TIE-2 ligand deficient cell, tissue, or animal. For example, and not by way of limitation, the recombinant TIE-2 ligand encoding gene may be engineered to contain an insertional mutation, for example the neo gene, which would inactivate the native TIE-2 ligand encoding gene. Such a construct, under the control of a suitable promoter, may be introduced into a cell, such as an embryonic stem cell, by a technique such as transfection, transduction, or injection. Cells containing the construct may then be selected by G418 resistance. Cells which lack an intact TIE-2 ligand encoding gene may then be identified, e.g. by Southern blotting, PCR detection, Northern blotting or assay of expression. Cells lacking an intact TIE-2 ligand encoding gene may then be fused to early embryo cells to generate transgenic animals deficient in such ligand. Such an animal may be used to define specific in vivo processes, normally dependent upon the ligand.

The present invention also provides for antibodies to the TIE-2 ligand described herein which are useful for detection of the ligand in, for example, diagnostic applications. For preparation of monoclonal antibodies directed toward this TIE-2 ligand, any technique which provides for the production of antibody molecules by continuous cell lines in culture may be used. For example, the hybridoma technique originally developed by Kohler and Milstein (1975, Nature 256: 495–497), as well as the trioma technique, the human B-cell hybridoma technique (Kozbor et al., 1983, Immunology Today 4: 72), and the EBV-hybridoma technique to produce human monoclonal antibodies (Cole et al., 1985, in "Monoclonal Antibodies and Cancer Therapy," Alan R. Liss, Inc. pp. 77–96) and the like are within the scope of the present invention.

The monoclonal antibodies for diagnostic or therapeutic use may be human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80: 7308–7312; Kozbor et al., 1983, Immunology Today 4: 72–79; Olsson et al., 1982, Meth. Enzymol. 92: 3–16). Chimeric antibody molecules may be prepared containing a mouse antigen-binding domain with human constant regions (Morrison et al., 1984, Proc. Natl. Acad. Sci. U.S.A. 81: 6851, Takeda et al., 1985, Nature 314: 452).

Various procedures known in the art may be used for the production of polyclonal antibodies to epitopes of the TIE-2 ligand described herein. For the production of antibody, various host animals can be immunized by injection with the TIE-2 ligand, or a fragment or derivative thereof, including but not limited to rabbits, mice and rats. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

A molecular clone of an antibody to a selected TIE-2 ligand epitope can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

The present invention provides for antibody molecules as well as fragments of such antibody molecules. Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent. Antibody molecules may be purified by known techniques, e.g., immunoabsorption or immunoaffinity chromatography, chromatographic methods such as HPLC (high performance liquid chromatography), or a combination thereof.

The present invention further encompasses an immunoassay for measuring the amount of TIE-2 ligand in a biological sample by a) contacting the biological sample with at least one antibody which specifically binds TIE-2 ligand so that the antibody forms a complex with any TIE-2 ligand present in the sample, and b) measuring the amount of the complex and thereby measuring the amount of the TIE-2 ligand in the biological sample.

The invention further encompasses an assay for measuring the amount of TIE-2 receptor in a biological sample by a) contacting the biological sample with at least one ligand of claim 1 so that the ligand forms a complex with the TIE-2 receptor, and b) measuring the amount of the complex and thereby measuring the amount of the TIE-2 receptor in the biological sample.

The present invention also provides for the utilization of the TIE-2 ligand to support the survival and/or growth and/or differentiation of TIE-2 receptor expressing cells. Thus, the ligand may be used as a supplement to support, for example, endothelial cells in culture Further, the discovery, by applicants, of the cognate ligand for the TIE-2 receptor enables the utilization of assay systems useful for the identification of agonists or antagonists of the TIE-2 receptor. For example, in one embodiment, antagonists of the TIE-2 receptor may be identified as test compounds that are capable of intefering with the interaction of the TIE-2 receptor and the TIE-2 ligand. Such agonists are identified by their ability to 1) block the binding of the TIE-2 ligand to the receptor, as measured, for example, using BIACORE; or 2) block the ability of the TIE-2 ligand to cause a biological response. Such biological activies include, but are not limited to, phosphorylation of the TIE-2 receptor or downstream components of the TIE-2 signal transduction pathway, or survival, growth or differentiation of TIE-2 receptor bearing cells.

In one embodiment, cells engineered to express the TIE-2 receptor may be dependent for growth on the addition of TIE-2 ligand. Such cells provide useful assay systems for identifying additional agonists of the TIE-2 receptor, or antagonists, capable of interfering with the activity of TIE-2 ligand on such cells. Alternatively, autocrine cells capable of co-expressing TIE-2 ligand and receptor may provide useful systems for assaying potential agonists or antagonists.

The TIE-2 receptor/TIE-2 ligand interaction also provides a useful system for identifying small molecule agonists or antagonists of the TIE-2 receptor. Fragments, mutants or derivatives of the TIE-2 ligand may be identified that bind the TIE-2 receptor but do not induce biological activity.

Alternatively, the characterization of the TIE-2 ligand enables the determination of active portions of the molecule. Further, the identification of the ligand enables the determination of the X-ray crystal structure of the receptor/ligand complex, thus enabling identification of the binding site on the receptor. Knowledge of the binding site will provide useful insight into the rational design of novel agonists and antagonists.

The specific binding of test agent to TIE-2 may be measured in a number of ways. For example, the actual binding of test agent to cells expressing tie-2 may be detected or measured, by detecting or measuring (i) test agent bound to the surface of intact cells; (ii) test agent cross-linked to TIE-2 protein in cell lysates; or (iii) test agent bound to TIE-2 in vitro. The specific interaction between test agent and TIE-2 may be evaluated by using reagents that demonstrate the unique properties of that interaction. For example, as a specific, nonlimiting example, the methods of the invention may be used as follows. Consider a case in which the TIE-2 ligand in a sample is to be measured. Varying dilutions of the sample (the test agent), in parallel with a negative control (NC) containing no TIE-2 ligand activity, and a positive control (PC) containing a known amount of TIE-2 ligand, may be exposed to cells that express tie-2 in the presence of detectably labeled TIE-2 ligand (in this example, radioiodinated ligand). The amount of TIE-2 ligand in the test sample may be evaluated by determining the amount of $^{125}$I-labeled TIE-2 ligand that binds to the controls and in each of the dilutions, and comparing the sample values to a standard curve. The more TIE-2 ligand in the sample, the less $^{125}$I-ligand that will bind to TIE-2. The amount of $^{125}$I-ligand bound may be determined by measuring the amount of radioactivity per cell, or by cross-linking the TIE-2 ligand to cell surface proteins using DSS, as described in Meakin and Shooter, 1991, Neuron 6: 153–163, and detecting the amount of labeled protein in cell extracts, using, for example, SDS polyacrylamide gel electrophoresis, which may reveal a labeled protein having a size corresponding to TIE-2 ligand/TIE-2 receptor. The specific test agent/TIE-2 interaction may further be tested by adding various dilutions of an unlabeled control ligand to the assays that does not bind the TIE-2 receptor and therefore should have no substantial affect on the competition between labeled TIE-2 ligand and test agent for TIE-2 binding. Alternatively, an agent known to be able to disrupt TIE-2 ligand/TIE-2 binding, such as, but not limited to, anti-TIE-2 antibody, or TIE-2 receptorbody as described herein, may be expected to interfere with the competition between $^{125}$I-TIE-2 ligand and test agent for TIE-2 receptor binding.

Detectably labeled TIE-2 ligand includes, but is not limited to, TIE-2 ligand linked covalently or noncovalently to a radioactive substance, a fluorescent substance, a substance that has enzymatic activity, a substance that may serve as a substrate for an enzyme (enzymes and substrates associated with colorimetrically detectable reactions are preferred) or to a substance that can be recognized by an antibody molecule that is preferably a detectably labeled antibody molecule.

Alternatively, the specific binding of test agent to TIE-2 may be measured by evaluating the secondary biological effects of TIE-2 ligand/TIE-2 receptor binding, including, but not limited to, cell growth and/or differentiation or immediate early gene expression or phosphorylation of TIE-2. For example, the ability of the test agent to induce differentiation can be tested in cells that lack tie-2 and in comparable cells that express tie-2; differentiation in tie-2-expressing cells but not in comparable cells that lack tie-2 would be indicative of a specific test agent/TIE-2 interaction. A similar analysis could be performed by detecting immediate early gene (e.g. fos and jun) induction in tie-2-minus and tie-2-plus cells, or by detecting phosphorylation of TIE-2 using standard phosphorylation assays known in the art. Such analysis might be useful in identifying agonists or antagonists that do not competitively bind to TIE-2.

Similarly, the present invention provides for a method of identifying an agent that has the biological activity of TIE-2 comprising (i) exposing a cell that expresses tie-2 to a test agent and (ii) detecting the specific binding of the test agent to TIE-2, in which specific binding to TIE-2 positively correlates with TIE-2 like activity. Specific binding may be detected by either assaying for direct binding or the secondary biological effects of binding, as discussed supra. Such a method may be particularly useful in identifying new members of the TIE ligand family or, in the pharmaceutical industry, in screening a large array of peptide and non-peptide agents (e.g., peptidomimetics) for TIE associated biological activity. In a preferred, specific, nonlimiting embodiment of the invention, a large grid of culture wells may be prepared that contain, in alternate rows, PC12 (or fibroblasts, see infra) cells that are either tie-2-minus or engineered to be tie-2-plus. A variety of test agents may then be added such that each column of the grid, or a portion thereof, contains a different test agent. Each well could then be scored for the presence or absence of growth and/or differentiation. An extremely large number of test agents could be screened for such activity in this manner.

In additional embodiments, the invention provides for methods of detecting or measuring TIE associated activity or identifying an agent as having such activity comprising (i) exposing a test agent to a TIE-2 protein in vitro under conditions that permit binding to occur and (ii) detecting binding of the test agent to the TIE-2 protein, in which binding of test agent to TIE-2 correlates with TIE-like activity. According to such methods, the TIE-2 may or may not be substantially purified, may be affixed to a solid support (e.g. as an affinity column or as an ELISA assay), or may be incorporated into an artificial membrane. Binding of test agent to TIE-2 may be evaluated by any method known in the art. In preferred embodiments, the binding of test agent may be detected or measured by evaluating its ability to compete with detectably labeled known TIE-2 ligands for TIE-2 binding.

The present invention also provides for a method of detecting the ability of a test agent compound to function as an antagonist of TIE-like activity comprising detecting the ability of the compound to inhibit an effect of TIE ligand binding to TIE-2 on a cell that expresses tie-2. Such an antagonist may or may not interfere with TIE-2/TIE-2 receptor binding. Effects of TIE-2 ligand binding to TIE-2 are preferably biological or biochemical effects, including, but not limited to, cell survival or proliferation, cell transformation, immediate early gene induction, or TIE-2 phosphorylation.

The present invention contemplates introduction of the TIE-2 receptor into cells that do not normally express this receptor, thus allowing these cells to exhibit profound and easily distinguishable responses to a ligand which binds this receptor. The present invention reveals that the type of response elicited depends on the cell utilized, and not the specific receptor introduced into the cell. Appropriate cell lines can be chosen to yield a response of the greatest utility for the assay, as well as discovery of, agents that can act on tyrosine kinase receptors. "Agents" refers to any molecule (s), including but not limited to peptide and non-peptide molecules, that will act in systems to be described in a receptor specific manner. One of the more useful systems to be exploited involves the introduction of the TIE-2 receptor into a fibroblast cell line (e.g., NIH3T3 cells) thus such a receptor which does not normally mediate proliferative responses can, following introduction into fibroblasts, nonetheless be assayed by a variety of well established methods to quantitate effects of fibroblast growth factors (e.g. thymidine incorporation or other types of proliferation assays; see van Zoelen, 1990, "The Use of Biological Assays For Detection Of Polypeptide Growth Factors" in Progress Factor Research, Vol. 2, pp. 131–152; Zhan and M. Goldfarb, 1986, Mol. Cell. Biol., Vol. 6, pp. 3541–3544). These assays have the added advantage that any preparation can be assayed both on the cell line having the introduced receptor as well as the parental cell line lacking the receptor; only specific effects on the cell line with the receptor would be judged as being mediated through the introduced receptor. Such cells may be further engineered to express the TIE-2 ligand, thus creating an autocrine system useful for assaying for molecules that act as antagonists/agonists of this interaction. Thus, the present invention contemplates host cells comprising nucleic acid encoding TIE-2 ligand and nucleic acid encoding TIE-2 receptor.

Because TIE-2 receptor has been identified in association with endothelial cells, and, as demonstrated herein, blocking of the ligand appears to prevent vascularization, applicants have demonstrated that the TIE-2 ligand will be useful for the induction of vascularization in diseases or disorders where such vascularization is indicated. Such diseases or disorders would include wound healing, ischaemia and diabetes. Antagonists of the TIE-2 receptor, such as receptor bodies as described herein in Examples 2 and 3, on the other hand, would be useful to prevent vascularization, thus preventing, for example, tumor growth.

The present invention also provides for pharmaceutical compositions comprising the TIE-2 ligands described herein, peptide fragments thereof, or derivatives in a pharmacologically acceptable vehicle. The TIE-2 ligand proteins, peptide fragments, or derivatives may be administered systemically or locally. Any appropriate mode of administration known in the art may be used, including, but not limited to, intravenous, intrathecal, intraarterial, intranasal, oral, subcutaneous, intraperitoneal, or by local injection or surgical implant. Sustained release formulations are also provided for.

EXAMPLE 1

Identification of the ABAE Cell Line as Reporter Cells for the TIE-2 Receptor

Adult BAE cells are registered in the European Cell Culture Repository, under ECACC#92010601. (See PNAS 75: 2621 (1978)). Northern (RNA) analyses revealed moderate levels of tie-2 transcripts in the ABAE (Adult Bovine Arterial Endothelial) cell line, consistent with in situ hybridization results that demonstrated almost exclusive localization of tie-2 RNAs to vascular endothelial cells. We therefore examined ABAE cell lysates for the presence of TIE-2 protein, as well as the extent to which this TIE-2 protein is tyrosine-phosphorylated under normal versus serum-deprived growth conditions. ABAE cell lysates were harvested and subjected to immunoprecipitation, followed by Western blot analyses of immunoprecipitated proteins with TIE-2 specific and phosphotyrosine-specific antisera. Omission or inclusion of TIE-2 peptides as specific blocking agents during TIE-2 immunoprecipitation allowed unambiguous identification of TIE-2 as a moderately detectable protein of ~150 kD whose steady-state phosphotyrosine levels diminish to near undetectable levels by prior serum-starvation of the cells.

Culture of ABAE cells and harvest of cell lysates was done as follows. Low-passage-number ABAE cells were plated as a monolayer at a density of $2 \times 10^6$ cells/150 mm plastic petri plate (Falcon) and cultured in Dulbecco's modified Eagle's medium (DMEM) containing 10% bovine calf serum (10% BCS), 2 mM L-glutamine (Q) and 1% each of penicillin and streptomycin (P-S) in an atmosphere of 5% $CO_2$. Prior to harvest of cell lysates, cells were serum-starved for 24 hours in DMEM/Q/P-S, followed by aspiration of the medium and rinsing of the plates with ice-cold phosphate buffered saline (PBS) supplemented with sodium orthovanadate, sodium fluoride and sodium benzamidine. Cells were lysed in a small volume of this rinse buffer that had been supplemented with 1% NP40 detergent and the protease inhibitors, PMSF and aprotinin. Insoluble debris was removed from the cell lysates by centrifugation at 14,000×G for 10 minutes, at 4° C. and the supernatants were subjected to immune-precipitation with antisera specific for TIE-2 receptor, with or without the presence of blocking peptides added to ~20 µg/ml lysate. Immunoprecipitated proteins were resolved by PAGE (7.5% Laemmli gel), and then electro-transferred to PVDF membrane and incubated either with various TIE-2- or phosphotyrosine-specific antisera. TIE-2-protein was visualized by incubation of the membrane with HRP-linked secondary antisera followed by treatment with ECL reagent (Amersham).

EXAMPLE 2

Cloning and Expression of TIE-2 Receptorbody for Affinity-Based Study of TIE-2 Ligand Interactions An expression construct was created that would yield a secreted protein consisting of the entire extracellular portion of the rat TIE-2 receptor fused to the human immunoglobulin gamma-1 constant region (IgG1 Fc). This fusion protein is called a TIE-2 "receptorbody" (RB), and would be normally expected to exist as a dimer in solution based on formation of disulfide linkages between individual IgG1 Fc tails. The Fc portion of the TIE-2 RB was prepared as follows. A DNA fragment encoding the Fc portion of human IgG1 that spans from the hinge region to the carboxy-terminus of the protein, was amplified from human placental cDNA by PCR with oligonucleotides corresponding to the published sequence of human IgG1; the resulting DNA fragment was cloned in a plasmid vector. Appropriate DNA restriction fragments from a plasmid encoding the full-length TIE-2 receptor and from the human IgG1 Fc plasmid were ligated on either side of a short PCR-derived fragment that was designed so as to fuse, in-frame, the TIE-2 and human IgG1 Fc protein-coding sequences. Thus, the resulting TIE-2 ectodomain-Fc fusion protein precisely substituted the IgG1 Fc in place of the region spanning the TIE-2 transmembrane and cytoplasmic domains. An alternative method of preparing RBs is described in Goodwin, et. al. Cell 73: 447–456 (1993).

Milligram quantities of TIE-2 RB were obtained by cloning the TIE-2 RB DNA fragment into the pVL1393 baculovirus vector and subsequently infecting the Spodoptera frugiperda SF-21AE insect cell line. Alternatively, the cell line SF-9 (ATCC Accession No. CRL-1711) or the cell line BTI-TN-5b1-4 may be used. DNA encoding the TIE-2 RB was cloned as an Eco RI-NotI fragment into the baculovirus transfer plasmid pVL1393.

Plasmid DNA purified by cesium chloride density gradient centrifugation was recombined into viral DNA by mixing 3 μg of plasmid DNA with 0.5 μg of Baculo-Gold DNA (Pharminigen), followed by introduction into liposomes using 30 μg Lipofectin (GIBCO-BRL). DNA-liposome mixtures were added to SF-21AE cells ($2\times10^6$ cells/60 mm dish) in TMN-FH medium (Modified Grace's Insect Cell Medium (GIBCO-BRL) for 5 hours at 27° C., followed by incubation at 27° C. for 5 days in TMN-FH medium supplemented with 5% fetal calf serum. Tissue culture medium was harvested for plaque purification of recombinant viruses, which was carried out using methods previously described (O'Reilly, D. R., L. K. Miller, and V. A. Luckow, *Baculovirus Expression Vectors—A Laboratory Manual*, 1992, New York: W. H. Freeman) except that the agarose overlay contained 125 μg/mL X-gal (5-bromo-4-chloro-3-indolyl-β-D-galactopyranoside; GIBCO-BRL). After 5 days of incubation at 27° C., non-recombinant plaques were scored by positive chromagenic reaction to the X-gal substrate, and their positions marked. Recombinant plaques were then visualized by addition of a second overlay containing 100 μg/mL MTT (3-[4,5-dimethylthiazol-2-yl]2,5, diphenyltetrazolium bromide; Sigma). Putative recombinant virus plaques were picked by plug aspiration, and purified by multiple rounds of plaque isolation to assure homogeneity. Virus stocks were generated by serial, low-multiplicity passage of plaque-purified virus. Low passage stocks of one virus clone (vTIE-2 receptor body) were produced.

SF-21AE cells were cultured in serum free medium (SF-900 II, Gibco BRL) containing 1X antibiotic/ antimycotic solution (Gibco BRL) and 25 mg/L Gentamycin (Gibco BRL). Pluronic F-68 was added as a surfactant to a final concentration of 1 g/L. Cultures (4L) were raised in a bioreactor (Artisan Cell Station System) for at least three days prior to infection. Cells were grown at 27° C., with gassing to 50% dissolved oxygen, at a gas flow rate of 80 mL/min (aeration at a sparge ring). Agitation was by means of a marine impeller at a rate of 100 rpm. Cells were harvested in mid-logarithmic growth phase ($\sim 2\times10^6$ cells per mL), concentrated by centrifugation, and infected with 5 plaque forming units of vTIE-2 Receptor Body per cell. Cells and inoculum were brought to 400 mL with fresh medium, and virus was adsorbed for 2 hours at 27° C. in a spinner flask. The culture was then resuspended in a final volume of 8 L with fresh serum-free medium, and the cells incubated in the bioreactor using the previously described conditions.

Culture medium from vTIE-2 Receptor Body-infected SF21AE cells were collected by centrifugation (500×g, 10 minutes) at 72 hours post-infection. Cell supernatants were brought to pH 8 with NaOH. EDTA was added to a final concentration of 10 mM and the supernatant pH was readjusted to 8. Supernatants were filtered (0.45 μm, Millipore) and loaded on a protein A column (protein A sepharose 4 fast flow or HiTrap protein A, both from Pharmacia). The column was washed with PBS containing 0.5M NaCl until the absorbance at 280 nm decreased to baseline. The column was washed in PBS and eluted with 0.5M acetic acid. Column fractions were immediately neutralized by eluting into tubes containing 1M Tris pH 9. The peak fractions containing the TIE-2 RB were pooled and dialyzed versus PBS.

EXAMPLE 3

Demonstration that TIE-2 has a Critical Role in Development of the Vasculature Given the absence of a known ligand for TIE-2 receptor, it was reasoned that it might be possible to gain insight into the function of TIE-2 by introduction of "excess" soluble TIE-2 receptor body (TIE-2 RB) into a developing system. The potential ability of TIE-2 RB to bind, and thereby neutralize, available TIE-2 ligand could result in an observable disruption of normal vascular development and characterization of the ligand. To examine whether TIE-2 RB could be used to disrupt vascular development in early chick embryos, small pieces of a biologically resorbable foam were soaked with TIE-2 RB and inserted immediately beneath the chorioallantoic membrane at positions just lateral to the primitive embryo.

Early chicken embryos develop atop the yolk from a small disk of cells that is covered by the chorioallantoic membrane (CAM). The endothelial cells that will come to line the vasculature in the embryo arise from both extra- and intra-embryonic cell sources. Extraembryonically-derived endothelial cells, which provide the major source for endothelial cells in the embryo, originate from accretions of mesenchyme that are situated laterally around the embryo-proper, just underneath the CAM. As these mesenchyme cells mature, they give rise to a common progenitor of both the endothelial and hematopoietic cell lineages, termed the hemangioblast. In turn, the hemangioblast gives rise to a mixed population of angioblasts (the endothelial cell progenitor) and hematoblasts (the pluripotential hematopoietic precursor). Formation of rudiments of the circulatory system begins when endothelial cell progeny segregate to form a one-cell-thick vesicle that surrounds the primitive blood cells. Proliferation and migration of these cellular components eventually produces a vast network of blood-filled microvessels under the CAM that will ultimately invade the embryo to join with limited, intraembryonically-derived vascular elements.

Figure 1B:
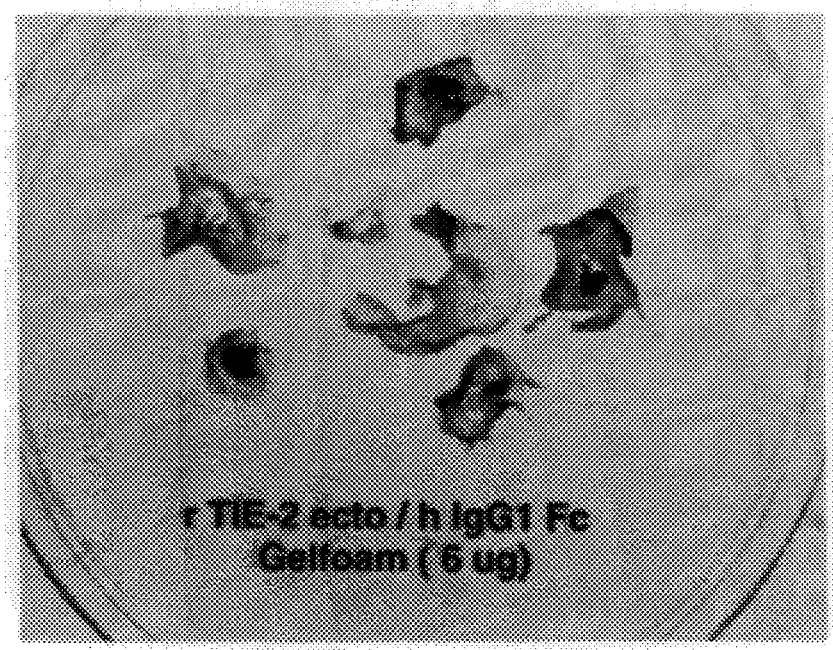

Newly fertilized chicken eggs obtained from Spafas, Inc. (Boston, Mass.) were incubated at 99.5° F., 55% RH. At about 24 hrs. of development, the egg shell was wiped down with 70% ethanol and a dentist's drill was used to make a 1.5 cm. hole in the blunt apex of each egg. The shell membrane was removed to reveal an air space directly above the embryo. Small rectangular pieces of sterile Gelfoam (Upjohn) were cut with a scalpel and soaked in equal concentrations of either TIE-2- or EHK-1 receptorbody. EHK-1 receptorbody was made as set forth in Example 2 using the EHK-1 extracellular domain instead of the TIE-2 extracellular domain (Maisonpierre et al., Oncogene 8: 3277-3288 (1993)). Each Gelfoam piece absorbed approximately 6 μg of protein in 30 μl. Sterile watchmakers forceps were used to make a small tear in the CAM at a position several millimeters lateral to the primitive embryo. The majority of the piece of RB-soaked Gelfoam was inserted under the CAM and the egg shell was sealed over with a piece of adhesive tape. Other similiarly-staged eggs were treated in parallel with RB of the unrelated, neuronally expressed receptor tyrosine kinase, EHK-1 (Maisonpierre et al., Oncogene 8: 3277-3288 (1993)). Development was allowed to proceed for 4 days and then the embryos were examined by visual inspection. Embryos were removed by carefully breaking the shells in dishes of warmed PBS and carefully cutting away the embryo with surrounding CAM. Of 12 eggs treated with each RB, 6 TIE-2 RB and 5 EHK-1 RB treated embryos had developed beyond the stage observed at the start of the experiment. A dramatic difference was seen between these developed embryos, as shown in FIGS. 1A and 1B. Those treated with EHK-1 RB appeared to have developed relatively normally. Four out of five EHK-1 embryos were viable as judged by the presence of a beating heart. Furthermore, the extra-embryonic vasculature, which is visually obvious due to the presence of red blood cells, was profuse and extended several centimeters laterally under the CAM. By contrast, those treated with TIE-2 RB were severely stunted, ranging from 2-5 mm. in diameter, as compared with more than 10 mm. in diameter for the EHK-1 RB embryos. All of the TIE-2 RB treated embryos were dead and their CAMs were devoid of blood vessels. The ability of TIE-2 RB to block vascular development in the chicken demonstrates that TIE-2 ligand is necessary for development of the vasculature.

EXAMPLE 4

Identification of a TIE-2-Specific Binding Activity in Conditioned Medium from the ras Oncogene-Transformed C2C12 Mouse Myoblast Cell Line Screening of ten-fold-concentrated cell-conditioned media (10X CCM) from various cell lines for the presence of soluble, TIE-2-specific binding activity (BIAcore ligand detection system, Pharmacia, Inc.) revealed binding activity in serum-free medium from oncogenic-ras-transformed C2C12 cells (C2C12-ras), RAT 2-ras (which is a ras transformed fibroblast cell line), human gliablastoma T98G and the human neuroblastoma cell line known as SHEP-1.

The C2C12-ras 10X CCM originated from a stably-transfected line of C2C12 myoblasts that was oncogenically transformed by transfection with the T-24 mutant of H-ras by standard calcium phosphate-based methods. An SV40 based neomycin-resistance expression plasmid was physically linked with the ras expression plasmid in order to permit selection of transfected clones. Resulting G418-resistant ras-C2C12 cells were routinely maintained as a monolayer on plastic dishes in DMEM/glutamine/penicillin-streptomycin supplemented with 10% fetal calf serum (FCS). Serum-free C2C12-ras 10X CCM was made by plating the cells at 60% confluence in a serum free defined media for 12 hours. (Zhan and Goldfarb, Mol. Cell. Biol. 6: 3541-3544 (1986)); Zhan, et al. Oncogene 1: 369-376 (1987)). The medium was discarded and replaced with fresh DMEM/Q/P-S for 24 hours. This medium was harvested and cells were refed fresh DMEM/Q/P-S, which was also harvested after a further 24 hours. These CCM were supplemented with the protease inhibitors PMSF (1 mM) and aprotinin (10 µg/ml), and ten-fold concentrated on sterile size-exclusion membranes (Amicon). TIE-2-binding activity could be neutralized by incubation of the medium with an excess of TIE-2 RB, but not by incubation with EHK-1 RB, prior to BIAcore analysis.

Purified TIE-2 RB was neutralized with 1M phosphate to a final pH of 6.8. Immediately prior to immobilization, the protein sample was adjusted to pH 8.3 using the coupling buffer (0.2M NaHCO$_3$ 0.5M NaCl). TIE-2 RB was immobilized on HiTrap NHS-activated Sepharose according to the manufacturer's specifications (Pharmacia Biotech, Piscataway, N.J.); final receptor density was 0.5 mg TIE-2 RB per mL of gel.

Conditioned medium from C2C12 ras cells was concentrated tenfold in a stirred cell fitted with a 3,000 Da MWCO membrane (Amicon; Danvers, Mass.). The concentrate was passed over Fractogel S cation exchange resin (EM Science; Gibbstown, N.J.). The resin was washed with two 100 mL aliquots of PBS which were combined subsequently with the flow through fraction and concentrated fivefold in a stirred cell. The concentrate was loaded onto TIE-2 receptor affinity columns (1 mL bed volume; 0.5 mg TIE-2 RB per mL of resin) at a flow rate of 0.5 mL/min. The column was washed with 5 mL of PBS followed by 5 mL of PBS containing 0.5M NaCl. The column was eluted with unbuffered 3M MgCl$_2$ (pH 3.8), and the eluted-peak fractions were neutralized immediately with 1M Hepes at pH 7.4. The peak fractions were assayed for specific binding activity using BIAcore biosensor technology (Pharmacia Biosensor; Piscataway, N.J.), and for purity by silver-staining of SDS-PAGE gels.

The MgCl$_2$-eluted fractions were pooled and concentrated sixfold using a 10,000 Da MWCO concentrator (Filtron; Northborough, Mass.). A 100-µL aliquot was injected onto a Superose 6 gel filtration column (Pharmacia; Piscataway, N.J.) and eluted with PBS containing 0.005% Tween 20 at 0.5 mL/min. The fractions (0.5 mL) were assayed for binding activity using BIAcore and identified and purified using SDS-PAGE under reducing and non-reducing conditions.

Binding activity of the TIE-2 RB affinity column and gel filtration column fractions was measured using BIAcore biosensor technology which monitors biomolecular interactions in real-time via surface plasmon resonance. Purified TIE-2 RB was covalently coupled through primary amines to the carboxymethyl dextran layer of a CM5 research grade sensor chip (Pharmacia Biosensor; Piscataway, N.J.). The sensor chip surface was activated using a mixture of N-hydroxysuccinimide (NHS) and N-ethyl-N'-(3-dimethylaminopropyl) carbodiimide (EDC), followed by immobilization of TIE-2 RB (25 µg/mL, pH 4.5) and deactivation of unreacted sites with 1.0M ethanolamine (pH 8.5). A negative control surface of the EHK-1 receptorbody was prepared in a similar manner.

The running buffer used in the system was HBS (10 mM Hepes, 3.4 mM EDTA, 150 mM NaCl, 0.005% P20 surfactant, pH 7.4). P20 surfactant (0.005%) was added to all of the fractions prior to BIAcore analysis. Aliquots of 45 µL were injected across the immobilized surface (either TIE-2 RB or EHK-1 RB) at a flow rate of 5 µL/min and the receptor binding was monitored for 9 min. The binding activity (resonance units, RU) was measured as the difference between a baseline value determined 30 s prior to the sample injection and a measurement taken at 30 s post-injection. Regeneration of the surface was accomplished with two 8-µL pulses of 3M MgCl$_2$.

The instrument noise level is 20 RU; therefore, any signal above 20 RU is considered evidence of protein interaction with the receptor. For C2C12-ras conditioned media, 3M MgCl$_2$ fractions from the TIE-2 affinity column (diluted sixfold with HBS running buffer in order to reduce the MgCl$_2$ concentration), and gel filtration fractions, the binding activities were in the range 30-1000 RU for the TIE-2 RB immobilized surface. For the same samples assayed on a EHK-1 RB immobilized surface, the measured activities were less than 20 RU. Specific binding to the TIE-2 receptorbody was evaluated further by incubating the samples with an excess of either soluble TIE-2 or EHK-1 RB prior to assaying the binding activity. The addition of soluble EHK-1 RB had no effect on the TIE-2 binding activity of any of the samples, while in the presence of soluble TIE-2 RB binding to the surface is less than 10 RU. Repeat assay with >50× concentrated C2C12-ras CCM medium repeat resulted in an at least two-fold enhancement over background of the TIE-2 specific binding signal.

EXAMPLE 5

C2C12-ras CCM Contains an Activity that Induces Tyrosine Phosphorylation of TIE-2 Receptor C2C12-ras 10X CCM was examined for its ability to induce tyrosine phosphorylation of TIE-2 in ABAE cells.

Serum-starved ABAE cells were briefly incubated with C2C12-ras CCM, lysed and subjected to immunoprecipitation and Western analyses as described above. Stimulation of serum-starved ABAE cells with serum-free C2C12-ras 10X CCM was done as follows. The medium of ABAE cells starved as described above was removed and replaced with either defined medium or 10X CCM that had been pre-warmed to 37° C. After 10 minutes, the media were removed and the cells were twice rinsed on ice with an excess of chilled PBS supplemented with orthovanadate/NaF/ benzamidine. Cell lysis and TIE-2-specific immunoprecipitation was done as described above.

ABAE cells incubated for 10 minutes with defined medium showed no induction of TIE-2 tyrosine phosphorylation, whereas incubation with C2C12-ras CCM stimulated at least a 100× increase in TIE-2 phosphorylation. This activity was almost totally depleted by pre-incubation of the C2C12-ras 10X CCM for 90 minutes at room temperature with 13 ug of TIE-2 RB coupled to protein G-Sepharose beads. Medium incubated with protein G Sepharose alone was not depleted of this phosphorylating activity.

EXAMPLE 6

Expression Cloning of TIE-2 Ligand

COS-7 cells were cultured in Dulbecco's modified Eagle's medium (DMEM) containing 10% fetal bovine serum (FBS), 1% each of penicillin and streptomycin (P/S) and 2 mM glutamine in an atmosphere of 5% $CO_2$. The rat myoblast C2C12 ras cell line was cultured in Eagle's minimal essential medium (EMEM) with 10% FBS, (P/S) and 2 mM glutamine.

Figure 2:
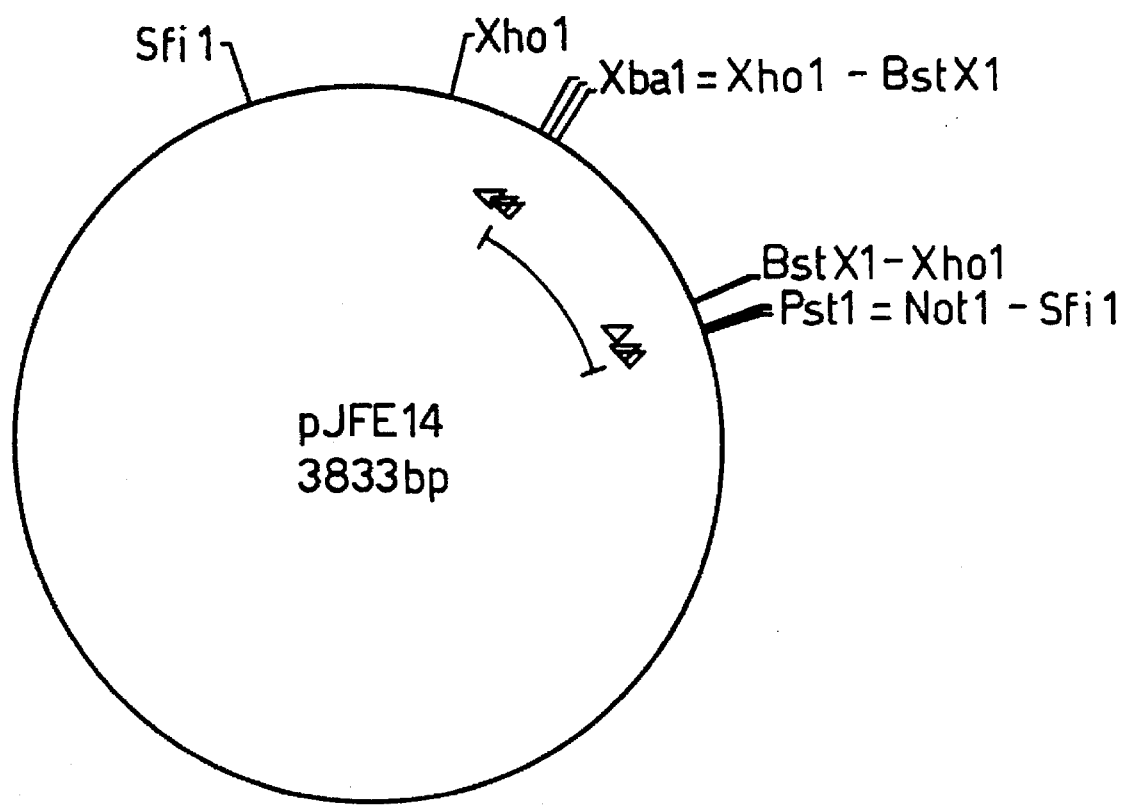
FIG. 2—Vector pJFE14.

Full length rat TIE-2 ligand cDNA clones were obtained by screening a C2C12 ras cDNA library in the pJFE14 vector expressed in COS cells. This vector, as shown in FIG. 2, is a modified version of the vector $pSR_\alpha$ (Takebe, et al. 1988, Mol. Cell. Biol. 8: 466–472). The library was created using the two BSTX1 restriction sites in the pJFE14 vector.

COS-7 cells were transiently transfected with either the pJFE14 library or control vector by the DEAE-dextran transfection protocol. Briefly, COS-7 cells were plated at a density of $1.0 \times 10^6$ cells per 100 mm plate 24 hours prior to transfection. For transfection, the cells were cultured in serum-free DMEM containing 400 µg/ml of DEAE-dextran, 1 µM chloroquine, and 2 mM glutamine, and 1 µg of the appropriate DNA for 3–4 hours at 37° C. in an atmosphere of 5% $CO_2$. The transfection media was aspirated and replaced with phosphate-buffered saline with 10% DMSO for 2–3 min. Following this DMSO "shock", the COS-7 cells were placed into DMEM with 10% FBS, 1% each of penicillin and streptomycin, and 2 mM glutamine for 48 hours.

Because the TIE-2 ligand is secreted it was necessary to permeabilize the cells to detect binding of the receptorbody probe to the ligand. Transfected COS-7 cells were plated at a density of $1.0 \times 10^6$ cells per 100 mm plate. The cells were rinsed with PBS and then incubated with PBS containing 1.8% formaldehyde for 15–30 min. at room temperature. Cells were then washed with PBS and incubated for 15 min. with PBS containing 0.1% Triton X-100 and 10% Bovine Calf Serum to permeabilize the cells and block non-specific binding sites.

The screening was conducted by direct localization of staining using a TIE-2 receptorbody, which consisted of the extracellular domain of TIE-2 fused to the IgG1 constant region. This receptorbody was prepared as set forth in Example 2. A 100 mm dish of COS cells was probed by incubating them for 30 min with TIE-2-RB. The cells were then washed twice with PBS, fixed with methanol, and then incubated for an additional 30 min with PBS/10% Bovine Calf Serum/anti-human IgG-alkaline phosphatase conjugate. After three PBS washes, cells were incubated in alkaline-phosphatase substrate for 30–60 min. The dish was then inspected microscopically for the presence of stained cells. For each stained cell a small area surrounding it was scraped from the dish using a plastic pipette tip and plasmid DNA was then rescued and used to electroporate bacterial cells. Plasmid DNA prepared from cultures derived from these electroporations was used to transfect COS cells for a second round of enrichment. The second round was performed with standard panning techniques. After the second round of enrichment, single bacterial colonies were picked and plasmid DNA prepared from these colonies was used to transfect COS-7 cells which were analyzed to confirm TIE-2 ligand expression as evidenced by binding to TIE-2 receptorbodies and phosphorylation of the TIE-2 receptor using the method set forth in Example 5.

DEPOSITS

The following have been deposited with the American Type Culture Collection, 12301 Parklawn Drive, Rockville, Md. 20852 in accordance with the Budapest Treaty. A plasmid clone encoding the TIE-2 ligand was deposited with the ATCC on Oct. 7, 1994 and designated as "pJFE14 encoding TIE-2 ligand" under ATCC Accession No. 75910. Recombinant *Autographa californica* baculovirus encoding the TIE-2 receptor body was deposited with the ATCC on Oct. 7, 1994 and designated as "vTIE-2 receptor body" under ATCC Accession No. VR2484.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. The plasmid designated pJFE14 encoding TIE-2 ligand (ATCC Accession No. 75910).

2. An isolated nucleic acid molecule comprising the nucleotide sequence encoding TIE-2 ligand contained in the plasmid designated as pJFE14 encoding TIE-2 ligand (ATCC Accession No. 75910).

3. An isolated nucleic acid molecule comprising a nucleotide sequence encoding TIE-2 ligand, wherein the nucleotide sequence is selected from the group consisting of:

(a) a nucleotide sequence comprising the coding region of the TIE-2 ligand contained in the vector designated as pJFE14 encoding TIE-2 ligand (ATCC Accession No. 75910); and (b) a nucleotide sequence that, as a result of the degeneracy of the genetic code, differs from the nucleotide sequence of (a) and encodes a TIE-2 ligand that binds TIE-2 receptor.

4. A vector which comprises the nucleic acid molecule of claim 3.

5. An expression vector comprising a nucleic acid molecule of claim 3, wherein the nucleic acid molecule is operatively linked to an expression control sequence.

6. A host-vector system for the production of TIE-2 ligand which comprises the expression vector of claim 5, in a suitable host cell.

7. The host-vector system of claim 6, wherein the suitable host cell is a bacterial cell, yeast cell, insect cell, or mammalian cell.

8. The host-vector system of claim 6, wherein the suitable host cell is a mammalian cell.

9. A method of producing TIE-2 ligand which comprises growing cells of the host-vector system of claim 6, under conditions permitting production of the ligand and recovering the ligand so produced.

10. A method of producing TIE-2 ligand which comprises growing cells of the host-vector system of claim 7, under conditions permitting production of the ligand and recovering the ligand so produced.

11. A method of producing TIE-2 ligand which comprises growing cells of the host-vector system of claim 8, under conditions permitting production of the ligand and recovering the ligand so produced.

* * * * *